United States Patent [19]

Revici

[11] Patent Number: 4,677,118

[45] Date of Patent: Jun. 30, 1987

[54] COMPOSITION AND METHOD FOR TREATMENT OF COPPER DEFICIENCY

[75] Inventor: Emanuel Revici, New York, N.Y.

[73] Assignee: Elena Avram, New York, N.Y.

[21] Appl. No.: 782,656

[22] Filed: Oct. 1, 1985

[51] Int. Cl.$^4$ ............ A61K 31/30; C07B 33/00; C07C 27/10; C11B 1/00
[52] U.S. Cl. ................................. 514/499; 260/398.6
[58] Field of Search ...................... 514/499; 260/398.6

[56] References Cited

U.S. PATENT DOCUMENTS 3,170,836  2/1965  Vergine .............................. 514/499
3,923,982  12/1975  Lamand et al. .................... 424/131

FOREIGN PATENT DOCUMENTS 676852  12/1963  Canada ................................ 514/499
77742   4/1983  European Pat. Off. ............ 260/414

Primary Examiner—Douglas W. Robinson
Attorney, Agent, or Firm—Pennie & Edmonds

[57] ABSTRACT

A method for making a composition containing a fatty acid or fatty ester compound and copper. The compositions produced by the method. Administration of these compositions to a patient to increase the copper content of cells or tissue having a copper deficiency or to treat at least some of the symptoms of diseases or adverse effects caused by this copper deficiency.

14 Claims, No Drawings

COMPOSITION AND METHOD FOR TREATMENT OF COPPER DEFICIENCY

TECHNICAL FIELD

The present disclosure concerns a method to treat various conditions resulting from copper deficiency and preparations for same.

BACKGROUND

It is known that the abnormal cells in general and the neoplastic cells in particular are poor in copper, a fact which is considered as including and enhancing their abnormal character. It is also known that the blood plasma of subjects with such abnormal conditions is especially rich in copper, apparently due to the body's attempt to correct the cellular copper deficiency. The form under which the copper is circulating in the blood, that is, mainly as ceruloplasmin, however, is not the proper form from which the copper can be taken by the abnormal cells.

SUMMARY OF THE INVENTION

The invention comprises novel compositions of fatty acids, ester, or oils which include copper incorporated therein. These composition are made by heating the oil component to a temperature of at least above 230° C. for a sufficient time to incorporate a predetermined amount of copper into the oil. At least about 0.1% can be used, although between 1 and 10% is preferred.

These compositions of the invention may be administered to a patient who has cells or tissue which are deficient in copper to increase tthe copper content as well as to treat the symptoms of diseases or adverse effects caused by the copper deficient cells or tissue.

DETAILED DESCRIPTION OF THE INVENTION

I have found that in general, the abnormal cells and tissues in the body have free lipids. Thus, a lipid or compound having a lipidic character introduced into the body can be selectively taken by the abnormal cells. Accordingly, it is believed that a copper compound having lipidic properties is useful as a therapeutic agent for patients who have such abnormal cells.

I have found that copper can be incorporated in the molecule of a fatty acid by heating together an organic or inorganic salt of copper with a fatty acid or its oil. Preferably, the fatty acid or oil is previously oxidized by being heated and mixed with air of oxygen. The mixtures of copper and fatty acids or oil are heated at a temperature above about 230° C. for a time until an exothermic reaction is observed, which reaction indicates that the incorporation is taking place.

Examples of the copper/fatty acid or oil compositions that can be used according to the invention include the reaction products of allylic unsaturated fatty acids or esters and a copper salt. These reaction products are produced by heating a liquid composition containing a fatty acid or fatty ester, structurally characterized by allylic unsaturation with a copper salt. Applicant believes that any copper salt is suitable for this invention. Preferably, the copper salt is an organic copper salt such as cupric acetate, and the liquid is preferably oxidized for example, by bubbling air or oxygen through the reaction mixture.

The allylically unsaturated compound is preferably a naturally occurring oil containing polyunsturated fatty esters, such as an animal, vegetable, or fish oil, and, particularly, polyunsaturated vegetable oils. Sesame oil, a vegetable oil consisting largely of triglycerides, is the most advantageous composition found to date in the practice of this invention.

The composition utilized should contain a significant percentage of molecular species having allylic moieties to render the compositions useful according to the invention. Such moieties are indicated by the following partial structures $-CH=CH-CH_2-CH=CH-$ and/or $-CH=CH-CH=CH-CH_2-$. As indicated, the unsaturation can be conjugated or nonconjugated, but the composition must contain allylic methylene hydrogen.

Such compositions may initially be oxidized or heated in the presence of air or oxygen at the temperature range between about 100° C. and about 150° C. The oxygen can be obtained by merely heating the composition in a vessel which is open to the atmosphere, but preferably and advantageously, the source of oxygen is a gas such as air which is injected into the heated oil. Introduction of air also provides a source of agitation.

The heating step is conducted for a period of from about 15 minutes to about two hours. The temperature should be maintained at an upper limit within the range of about 230° C. to 250° C., and preferably about 235° C. to 240° C. These temperature limitations are based on a heating time of about one-half hour. The temperatures can be altered within limits depending on the time of heating For example, when the temperature is about 235° C., the time is about one-half hour, while temperatures as high as 250° C. require a shorter period of time for heating. Higher temperatures for a prolonged period of time tend to degrade the composition and should thus be avoided.

Agitation, by stirring for example, aids in the reaction, and experiments to date indicate that a fairly violent stirring is advantageous. The introduction of air into the mixture during the heating is also very advantageous, particularly when the mixture is not subjected to prolonged heating and thus, is the preferred method. The mixing or stirring can be accomplished with the introduction of the air.

After the reaction has taken place, the mixture is cooled. The remaining fluid is ready for use after appropriate sterilization for injection or incorporated into capsules, such as gelatin, for oral administration.

The precise nature of the compositions which result from the above-described treatment or the identity of the effective component or components is not presently known. It is known, however, that these compositions do include copper and that a proportion of copper in the range of about 1 to 10 weight percent has been found to be effective.

As mentioned above, although any copper salt may be used, an organic salt of copper, such as cupric acetate, is preferred, with the copper bonding the eleostearic acid present in this oil. Although any amount above 0.1% of copper incorporated into the composition is useful, the preferred amount ranges between about 1 to 10 weight percent.

The products obtained have the copper incorporated in general at the level of the double bonds of the different unsaturated fatty acids, this causes their toxicity to be exceptionally low. The injection of 1 ml of a product having 5% copper to a mouse does not kill it.

The incorporated copper composition may be administered orally, by injections, sublingually or rectally in the appropriate formulation.

The incorporated copper is believed to be absorbed by the abnormal cells, thus compensating for their low copper content. This treatment produces objective and subjective improvement in the conditions, of patients having a variety of diseases based upon such abnormal cells. The neoplastic diseases are examples of diseased in which low cellular copper abnormal cells are found.

Such low cellular copper abnormal cells are believed to cause an anabolic imbalance in the body. This anabolic imbalance can be analyzed and diagnosed by blood and urine analyses. An eosinophilia (above 100/cmm), a low red cell sedimentation rate (below 15 ml/1 hour), a low serum potassium (below 4.5 mEq), a urinary alkaline pH (above 7), low specific gravity (below 1.016), high surface tension (above 89 dynes/cm), and high calcium or chloride excretion are indications of an anabolic imbalance. (The opposite analyses would indicate a catabolic imbalance.)

These analyses and clinical manifestations have to be changed by the administration of the incorporated copper compound. In a 5% copper incorporated preparation, amounts from about 2 to 10 ml daily are predilectly used for the treatment of this anabolic imbalance. For the neoplastic conditions wwith catabolic imbalances, low doses from 1/10 to 2 ml daily are predilectly used. In general the higher the dose used, the better are the clinical results.

Interesting results are those concerning pain, the changes induced in the lesions manifesting first an action upon pain. Manifest changes in the tumors and in the subjective manifestations of the neoplastic diseases are obtained even in a very short time. Thus, the incorporated copper appears as a predilect treatment of the symptoms of neoplastic conditions, and possibly to the treatment of such condition themselves.

Good results were also obtained in the use of the incorporated copper compounds for the different manifestations of AIDS (acquired immune deficiency syndrome) as well as for thee ARC (AIDS related complex).

Interesting also are the results in almost all the different conditions, such as neurological conditions, epilepsy and others, the problem of cellular copper deficiency being a general pathological occurrence. Interesting is the action of the lipidic copper products on the viral infections.

The incorporated copper composition may be administered together with different other agents.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method of preparing a a copper and oil reaction product for pharmaceutical use which comprises heating a mixture of an animal, vegetable or fish oil having an allylic unsaturation of the type $-CH=CH-CH_2-CH=CH-$ or $-CH=CH-CH=CH-CH_2-$ and an organic copper salt at a temperature of between about 230° and 250° C. for between about 15 minutes and 2 hours to incorporate by exothermic reaction between about 0.1 and 10% by weight copper into the oil.

2. The method of claim 1 wherein the oil is oxidized before the copper compound is added by mixing the oil with air and heating the mixture.

3. The method of claim 1 wherein the mixture is oxidized by introducing air into the mixture while heating at the stated temperature and time ranges.

4. The copper and oil reaction product produced by the method of claim 1.

5. A method for increasing the copper content of cells or tissue having a copper deficiency which comprises administering to a patient having said copper deficient cells or tissue a therapeutically effective amount of the composition of claim 4.

6. The method of claim 5 wherein about 1/10 to 10 ml of the composition is daily administered to the patient.

7. A method of preparing a copper and oil reaction product for pharmaceutical use which comprises:
   oxidizing an unsaturated vegetable oil by heating a mixture of air and the oil; and
   mixing said oxidized vegetable oil with an organic copper salt at a temperature of between about 230 and 250° C. for about one-half hour to incorporate by exothermic reaction between about 1 and 10% by weight copper into the oil.

8. The copper and oil reaction product produced by the method of claim 4.

9. A method for increasing the copper content of cells or tissue having a copper deficiency which comprises administering to a patient having said copper deficient cells or tissue a therapeutically effective amount of the composition of claim 8.

10. The method of claim 9 wherein about 1/10 to 10 ml of the composition is daily administered to the patient.

11. A method of preparing a copper and oil reaction product for pharmaceutical use which comprises: heating sesame seed oil, air and cupric acetate at a temperature of between about 235 and 240° C. for about one-half hour with agitation to incorporate by exothermic reaction about 1% by weight copper into the oil.

12. The copper and oil reaction product produced by the method of claim 11.

13. A method for increasing the copper content of cells or tissue having a copper deficiency which comprises administering to a patient having said copper deficient cells or tissue a therapeutically effective amount of the composition of claim 12.

14. The method of claim 13 wherein about 1/10 to 10 ml of the composition is daily administered to the patient.

* * * * *